United States Patent [19]

Zurflüh

[11] Patent Number: 5,015,640
[45] Date of Patent: May 14, 1991

[54] 5,7-DIHYDRO-6H DIBENZ[C,E]AZEPINE-6-(THIO)CARBOXIMIDIC ACID ESTERS AND PESTICIDAL USE THEREOF

[75] Inventor: René Zurflüh, Bülach, Switzerland

[73] Assignee: Ciba-Geigy Corporation, Ardsley, N.Y.

[21] Appl. No.: 433,071

[22] Filed: Nov. 7, 1989

[30] Foreign Application Priority Data

Nov. 11, 1988 [CH] Switzerland ............... 4191/88
Aug. 24, 1989 [CH] Switzerland ............... 3067/89

[51] Int. Cl.⁵ .................. C07D 223/18; A01N 47/42
[52] U.S. Cl. .................................. 514/217; 540/587
[58] Field of Search ...................... 540/587; 514/217

[56] References Cited
U.S. PATENT DOCUMENTS
4,766,115 8/1988 Bruderer et al. ............... 540/587

OTHER PUBLICATIONS
Chemical Abstracts, vol. 106, No. 5, Abstract 32873k, p. 533, Feb. 2, 1987.

Primary Examiner—Frederick E. Waddell
Assistant Examiner—Zinna Northington-Davis
Attorney, Agent, or Firm—Edward McC. Roberts

[57] ABSTRACT

The invention relates to compounds of the formula

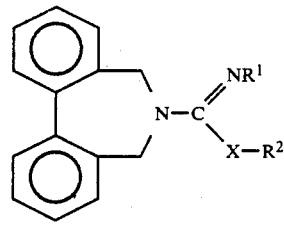

wherein $R^1$, $R^2$ and X have the significances given herein, their acid addition salts and the preparation of these substances, pest control compositions which contain these substances as active ingredients and the use of the active substances or compositions for the control of pests.

27 Claims, No Drawings

5,7-DIHYDRO-6H DIBENZ[C,E]AZEPINE-6-(THIO)CARBOXIMIDIC ACID ESTERS AND PESTICIDAL USE THEREOF

BRIEF SUMMARY OF THE INVENTION

The invention relates to heterocyclic compounds, namely 5,7-dihydro-6H-dibenz[c,e]azepine-6-(thio)carboximidic acid esters of the formula

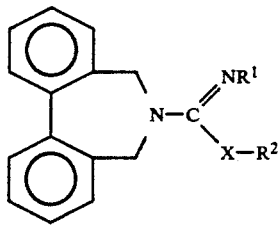

I wherein
$R^1$ is hydrogen or $-Y-R^3$,
$R^2$ is $C_{1-6}$-alkyl, $C_{3-6}$-alkenyl or $C_{3-6}$-alkynyl substituted with $C_{3-6}$—cycloalkyl, aryl, aryloxy or heteroaryl, with the substitution being optional when $R^1$ is $-Y-R^3$, or
$R^2$ is unsubstituted $C_{2-6}$-alkyl or $C_{2-6}$-alkyl substituted with aryl or aryloxy and which is interrupted by one or two oxygen atoms, or
$R^2$ is aryl, heteroaryl, 2-tetrahydrofuranylmethyl, 2-tetrahydropyranylmethyl or one of the groups (a) to (c)

$-N=CR^4R^5$                          (a)

$-Z-ON=CR^4R^5$                 (b)

$-Z-NR^6R^7$                         (c)

$R^3$ is hydrogen; unsubstituted or substituted $C_{1-6}$-alkyl, $C_{2-6}$-alkenyl, $C_{2-6}$-alkynyl, $C_{3-6}$-cycloalkyl, phenyl, naphthyl, p-biphenylyl, benzylphenyl, phenoxyphenyl, benzoylphenyl, 3,4-methylenedioxyphenyl or five- to six-membered heterocyclyl; a group $-OR^8$ (d); or a group $-NR^9R^{10}$ (e),
$R^4$ is $C_{1-6}$-alkyl,
$R^5$ is $C_{1-6}$-alkyl or phenyl, or
$R^4$ and $R^5$ taken together are tetra-, penta- or hexamethylene,
$R^6$ is hydrogen or $C_{1-4}$-alkyl,
$R^7$ is $C_{1-4}$-alkyl, $C_{2-5}$-alkanoyl or $C_{2-5}$-alkoxycarbonyl,
or
$R^6$ and $R^7$ taken together with the nitrogen atom to which they are attached are a five- to seven-membered unsubstituted heterocyclic group or which is substituted with one or two $C_{1-4}$-alkyl groups and which, in addition to the nitrogen can also have an additional 1 or 2 hetero atoms selected from oxygen, sulfur and nitrogen, and/or a keto function in the ring,
$R^8$ is $C_{1-6}$-alkyl, $C_{2-6}$-haloalkyl, $C_{3-6}$-alkenyl, $C_{3-6}$-alkynyl, benzyl or unsubstituted or substituted phenyl,
$R^9$ is hydrogen or $C_{1-4}$-alkyl,
$R^{10}$ is $C_{1-6}$-alkyl or unsubstituted or substituted phenyl, X is oxygen or sulfur, provided that when $R^2$ is group (a), X is oxygen,
Y is carbonyl, sulfinyl or sulfonyl, provided that when $R^3$ is hydrogen or a group (d) or (e), Y is carbonyl, and
Z is $C_{1-4}$-alkylene, as well as acid addition salts of the compounds of formula I in which $R^1$ is hydrogen.

The compounds in accordance with the invention, that is, the compounds of formula I and the acid addition salts mentioned above, are pest control agents which are especially suitable for the control of insects, nematodes and mites, for example, spider mites. Accordingly, the invention also embraces pest control compositions which contain compounds in accordance with the invention as the active substance, a process for the preparation of these compounds as well as the use of these compounds or compositions for the control of pests.

DETAILED DESCRIPTION OF THE INVENTION

The invention relates to 5,7-dihydro-6H-dibenz[c,e]azepine-6-(thio)carboximidic acid esters of the formula

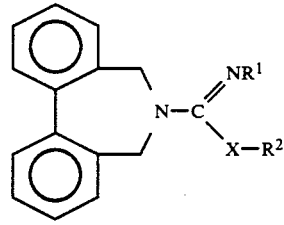

I wherein
$R^1$ is hydrogen or $-Y-R^3$,
$R^2$ $C_{1-6}$-alkyl, $C_{3-6}$-alkenyl or $C_{3-6}$-alkynyl substituted with $C_{3-6}$ cycloalkyl, aryl, aryloxy or heteroaryl, with the substitution being optional when $R^1$ is $-Y-R^3$, or
$R^2$ is $C_{2-6}$-alkyl which can be substituted with aryl or aryloxy and which is interrupted by one or two oxygen atoms, or
$R^2$ is aryl, heteroaryl, 2-tetrahydrofuranylmethyl, 2-tetrahydropyranylmethyl or one of the groups (a) to (c)

$-N=CR^4R^5$                          (a)

$-Z-ON=CR^4R^5$                 (b)

$-Z-NR^6R^7$                         (c)

$R^3$ is hydrogen; unsubstituted or substituted $C_{1-6}$-alkyl, $C_{2-6}$-alkenyl, $C_{2-6}$-alkynyl, $C_{3-6}$-cycloalkyl, phenyl, naphthyl, p-biphenylyl, benzylphenyl, phenoxyphenyl, benzoylphenyl, 3,4-methylenedioxyphenyl or five- to six-membered heterocyclyl; a group $-OR^8$ (d); or a group $-NR^9R^{10}$ (e),
$R^4$ is $C_{1-6}$-alkyl,
$R^5$ is $C_{1-6}$-alkyl or phenyl, or
$R^4$ and $R^5$ taken together are tetra-, penta- or hexamethylene,
$R^6$ is hydrogen or $C_{1-4}$-alkyl,
$R^7$ is $C_{1-4}$-alkyl, $C_{2-5}$-alkanoyl or $C_{2-5}$-alkoxycarbonyl, or $R^6$ and $R^7$ together with the nitrogen atom to which they are attached are a five- to seven-membered unsubstituted heterocyclic group or which is substituted with one or two $C_{1-4}$-alkyl groups and which, in addition to the nitrogen atom, can also have an additional 1 or 2 hetero atoms selected from oxygen, sulfur and nitrogen and/or a keto function in the ring, $R^8$ is $C_{1-6}$-alkyl, $C_{2-6}$-haloalkyl, $C_{3-6}$-alkenyl, $C_{3-6}$-alkynyl, benzyl or unsubstituted or substituted phenyl, $R^9$ is hydrogen or $C_{1-4}$-alkyl, $R^{10}$ is $C_{1-6}$-alkyl or unsubstituted or substituted phenyl, X is oxygen or sulfur, provided that when $R^2$ is group (a), X is oxygen, Y is carbonyl, sulfinyl or sulfonyl, provided that when $R^3$ is hydrogen or a group (d) or (e), Y is carbonyl, and Z is $C_{1-4}$-alkylene, as well as acid addition salts of the compounds of formula I in which $R^1$ is hydrogen.

The compounds in accordance with the invention, that is, the compounds of formula I and the acid addition salts mentioned above, are pest control agents which are especially suitable for the control of insects, nematodes and mites, for example, spider mites. Accordingly, the invention also embraces pest control compositions which contain compounds in accordance with the invention as the active substance, a process for the preparation of these compounds as well as the use of these compounds or compositions for the control of pests.

As used herein, "alkyl", "alkenyl", "alkynyl" and "alkylene" are straight-chain or branched aliphatic radicals Moreover, the alkenyl and alkynyl residues can have more than one double or triple bond, respectively. A halogen atom which may be present can be fluorine, chlorine, bromine or iodine. A group such as, for example, alkyl, alkenyl, alkynyl, aryl or heteroaryl, as such or as part of a larger group, which carries two or more halogen substituents can have the same or different halogen atoms As aryl or aryloxy there are to be understood preferably phenyl and naphthyl, and phenoxy and naphthyloxy, respectively, and as heteroaryl there are to be understood preferably heterocyclic groups having aromatic character such as pyridyl, furyl and thienyl as well as groups having a fused benzene ring, for example, quinolinyl and quinoxalinyl. The aryl, aryloxy and heteroaryl groups can bear one or more substituents. Exemplary of such substituents for aryl, aryloxy or heteroaryl when this itself is a substituent on a $C_{1-6}$-alkyl, $C_{3-6}$-alkenyl or $C_{3-6}$-alkynyl ($R^2$), are one or two substituents selected from the group consisting of halogen, $C_{1-6}$-alkyl, $C_{1-4}$-haloalkyl, $C_{1-4}$-alkoxy, $C_{1-4}$-haloalkoxy, $C_{1-4}$-alkylthio, $C_{1-4}$-haloalkylthio, nitro, cyano, phenyl and phenoxy. When $R^2$ is substituted aryl or heteroaryl, the substituents are suitably one or two substituents selected from the group consisting of halogen, $C_{1-4}$- alkyl, $C_{1-4}$-haloalkyl, $C_{1-4}$-alkoxy, $C_{1-4}$- haloalkoxy, $C_{1-4}$-alkylthio, $C_{1-4}$-haloalkylthio, nitro and cyano. As substituents for $C_{3-6}$-cycloalkyl, there come into consideration up to 4 substituents selected from the group consisting of halogen, $C_{1-4}$-alkyl and $C_{1-4}$-alkoxy. In this case, a halogen substituent which may be present is preferably fluorine or chlorine. When $R^3$ is substituted $C_{1-6}$-alkyl, $C_{2-6}$-alkenyl or $C_{2-6}$-alkynyl, the alkyl, alkenyl or alkynyl residue can be suitably independently mono- or multiply-substituted with halogen, $C_{1-4}$-alkoxy, cyano, or unsubstituted or substituted phenyl or phenoxy. In the case of the just-mentioned unsubstituted or substituted phenyl or phenoxy as well as in the case of unsubstituted or substituted phenyl, naphthyl, p-biphenylyl, benzylphenyl, phenoxyphenyl, benzoylphenyl or 3,4-methylenedioxyphenyl mentioned as a meaning for $R^3$ itself, there come into consideration aromatic groups which are unsubstituted or independently mono- to tri-substituted with halogen, $C_{1-4}$-alkyl, $C_{1-4}$-haloalkyl, $C_{1-4}$-alkoxy, $C_{1-4}$-haloalkoxy, $C_{1-4}$-alkylthio, $C_{1-4}$-haloalkylthio, nitro, cyano, amino, $C_{1-4}$-alkylamino, di($C_{1-4}$-alkyl)amino, carboxy or $C_{2-5}$-alkoxycarbonyl. This also applies to $R^8$ and $R^{10}$ as unsubstituted or substituted phenyl. As five- to six-membered heterocyclyl, there are to be understood such heterocyclic groups which, in addition to ring carbon atoms, can have 1 to 3 hetero atoms selected from the group consisting of nitrogen, oxygen and sulfur in the ring and which are aromatic, partially saturated or completely saturated. Heterocyclic groups with a fused benzene ring also come into consideration. The heterocyclic groups can be unsubstituted or substituted with 1 to 2 halogen atoms, 1 cyano group, 1 $C_{1-4}$-alkyl residue, 1 $C_{1-4}$-haloalkyl residue and/or 1 $C_{1-4}$-alkoxy group, and when a fused benzene ring is present this, in turn, can be substituted with one or more substituents selected from halogen, methyl, methoxy and trifluoromethyl. Pyridyl, pyrrolyl, piperidinyl, pyrazinyl, imidazolyl, 1,2,4-triazolyl, furyl, thiophenyl, morpholinyl, quinolinyl and benzofuryl are examples of such heterocyclyl groups.

When asymmetric carbon atoms are present in the compounds of formula I, the compounds occur in optically active form. In the case of those compounds of formula I in which aliphatic double bonds are present, geometric isomerism can also occur. In any event, the compounds of formula I occur in the [E]- or [Z]-form because of the presence of the imino double bond. Furthermore, atropic isomerism can occur. Formula I is accordingly intended to embrace all of the possible isomeric forms as well as their mixtures, for example, racemic mixtures and any [E/Z] mixtures.

As acid addition salts of the compounds of formula I there come into consideration physiologically compatible salts. The compounds of formula I form salts with inorganic and organic acids, preferably hydrohalic acids such as hydrochloric acid and hydrobromic acid; nitric acid; phosphoric acid; sulfuric acid; mono- and bifunctional carboxylic acids and hydroxycarboxylic acids such as acetic acid, maleic acid, succinic acid, fumaric acid, tartaric acid, citric acid, salicylic acid, sorbic acid and lactic acid; and sulfonic acids such as 1,5-naphthalene-disulfonic acid.

A special group of compounds of formula I consists of those compounds of formula I, wherein $R^1$, $R^2$ and X have the same significances as hereinbefore and $R^3$ is hydrogen; unsubstituted or substituted $C_{1-6}$-alkyl, $C_{3-6}$-alkenyl, $C_{3-6}$-alkynyl, $C_{3-6}$-cycloalkyl, phenyl, naphthyl, p-biphenylyl, benzylphenyl, phenoxyphenyl, benzoylphenyl or five- to six-membered heterocyclyl; a group —$OR^8$ (d) in which $R^8$ is $C_{1-6}$-alkyl or unsubstituted or substituted phenyl; or a group —$NR^9R^{10}$ (e), in which $R^9$ and $R^{10}$ have the significances given hereinbefore.

$R^1$ preferably is a group —Y—$R^3$ and X preferably is oxygen. In the case of the compounds I in which $R^1$ is hydrogen, $R^2$ is preferably a group (b) or (c) in which Z is ethylene, while in the compounds of formula I in which $R^1$ is a group $-Y-R^3$, $R^2$ preferably is $C_{1-6}$-alkyl, especially $C_{1-4}$-alkyl, and independently thereof $R^3$ preferably is unsubstituted or substituted phenyl, unsubstituted or substituted five- to six-membered heterocyclyl or a group (d) and Y preferably is carbonyl.

Preferred compounds of formula I are:

2-[(Isopropylideneamino)oxy]-ethyl 5,7-dihydro-6H-dibenz[c,e]azepine-6-carboximidate, 2-ethoxycarbonylamino-ethyl 5,7-dihydro-6H-dibenz[c,e]azepine-6-carboximidate, ethyl N-benzoyl-5,7-dihydro-6H-dibenz[c,e]azepine-6-carboximidate, ethyl N-(p-chlorobenzoyl)-5,7-dihydro-6H-dibenz[c,e]-azepine-6-carboximidate, ethyl N-isonicotinoyl-5,7-dihydro-6H-dibenz[c,e]azepine-6-carboximidate, ethyl N-ethoxycarbonyl-5,7-dihydro-6H-dibenz[c,e]azepine-6-carboximidate, ethyl N-(1-imidazolylcarbonyl)-5,7-dihydro-6H-dibenz[c,e]azepine-6-carboximidate, ethyl N-(p-bromobenzoyl)-5,7-dihydro-6H-dibenz[c,e]-azepine-6-carboximidate, ethyl N-(p-tert.butylbenzoyl)-5,7-dihydro-6H-dibenz[c,e]azepine-6-carboximidate ethyl N-(p-fluorobenzoyl)-5,7-dihydro-6H-dibenz[c,e]-azepine-6-carboximidate, ethyl N-methoxycarbonyl-5,7-dihydro-6H-dibenz[c,e]-azepine-6-carboximidate, cyclopropylmethyl 5,7-dihydro-6H-dibenz[c,e]azepine-6-carboximidate, ethyl N-(p-trifluoromethylbenzoyl)-5,7-dihydro-6H-dibenz[c,e]azepine-6-carboximidate, ethyl N-(p-anisoyl)-5,7-dihydro-6H-dibenz[c,e]azepine-6-carboximidate, methyl N-benzoyl-5,7-dihydro-6H-dibenz[c,e]azepine-6-carboximidate, propyl N-benzoyl-5,7-dihydro-6H-dibenz[c,e]azepine-6-carboximidate, ethyl N-(2-furoyl)-5,7-dihydro-6H-dibenz[c,e]azepine-6-carboximidate and ethyl N-cyclopropylcarbonyl-5,7-dihydro-6H-dibenz[c,e]azepine-6-carboximidate, of which the 1st, 3rd, 6th, 10th and 11th compounds are especially preferred.

Representatives of the compounds of formula I are also the following:

2-(2-phenoxyethoxy)-ethyl 5,7-dihydro-6H-dibenz[c,e]-azepine-6-carboximidate, 3-pyridylmethyl 5,7-dihydro-6H-dibenz[c,e]azepine-6-carboximidate, 2-piperidino-ethyl 5,7-dihydro-6H-dibenz[c,e]azepine-6-carboximidate, 2-[(1-ethylpentylideneamino)oxy]-ethyl 5,7-dihydro-6H-dibenz[c,e]azepine-6-carboximidate, 2-[(cyclohexylideneamino)oxy]-ethyl 5,7-dihydro-6H-dibenz[c,e]azepine-6-carboximidate, 2-(N-methyl-methoxycarbonylamino)-ethyl 5,7-dihydro-6H-dibenz[c,e]azepine-6-carboximidate, 2-methoxycarbonylamino-propyl 5,7-dihydro-6H-dibenz[c,e]azepine-6-carboximidate, methoxycarbonylaminomethyl 5,7-dihydro-6H-dibenz[c,e]-azepine-6-carboximidate, ethyl N-(2-picolinoyl)-5,7-dihydro-6H-dibenz[c,e]azepine-6-carboximidate, ethyl N-formyl-5,7-dihydro-6H-dibenz[c,e]azepine-6-carboximidate, ethyl N-phenylethynyl-5,7-dihydro-6H-dibenz[c,e]azepine-6-carboximidate, ethyl N-(1-piperidinecarbonyl)-5,7-dihydro-6H-dibenz[c,e]azepine-6-carboximidate, ethyl N-(1,2,4-triazolyl-1-carbonyl)-5,7-dihydro-6H-dibenz[c,e]-azepine-6-carboximidate, ethyl N-(o-methoxybenzoyl)-5,7-dihydro-6H-dibenz[c,e]-azepine-6-carboximidate, methyl N-(p-chlorobenzoyl)-5,7-dihydro-6H-dibenz[c,e]-azepine-6-carboximidate, propyl N-(p-chlorobenzoyl)-5,7-dihydro-6H-dibenz[c,e]-azepine-6-carboximidate, isopropyl N-(p-chlorobenzoyl)-5,7-dihydro-6H-dibenz[c,e]azepine-6-carboximidate, ethyl N-(p-iodobenzoyl)-5,7-dihydro-6H-dibenz[c,e]-azepine-6-carboximidate, phenyl 5,7-dihydro-6H-dibenz[c,e]azepine-6-carboximidate, cyclohexanone O-[(5,7-dihydro-6H-dibenz[c,e]azepin-6-yl)carboximidoyl] oxime, acetophenone O-[(5,7-dihydro-6H-dibenz[c,e]azepin-6-yl)-carboximidoyl] oxime, 2-dimethylaminoethyl 5,7-dihydro-6H-dibenz[c,e]-azepine-6-carboximidate, 2-ethylcarbonylamino-ethyl 5,7-dihydro-6H-dibenz[c,e]-azepine-6-carboximidate, ethyl N-propargyloxycarbonyl-5,7-dihydro-6H-dibenz[c,e]azepine-6-carboximidate, ethyl N-(2-chloroisonicotinoyl)-5,7-dihydro-6H-dibenz[c,e]azepine-6-carboximidate, ethyl N-(2-cyanoisonicotinoyl)-5,7-dihydro-6H-dibenz[c,e]azepine-6-carboximidate, ethyl N-(6-chloronicotinoyl)-5,7-dihydro-6H-dibenz[c,e]-azepine-6-carboximidate, ethyl N-(p-benzylbenzoyl)-5,7-dihydro-6H-dibenz[c,e]-azepine-6-carboximidate, ethyl N-(p-benzoylbenzoyl)-5,7-dihydro-6H-dibenz[c,e]-azepine-6-carboximidate, ethyl N-[p-(p-chlorophenoxy)benzoyl]-5,7-dihydro-6H-dibenz[c,e]azepine-6-carboximidate, and 2-[(1-methylisobutylideneamino)oxy]-ethyl 5,7-dihydro-6H-dibenz[c,e]azepine-6-carboximidate.

The processes in accordance with the invention for the preparation of the compounds of formula I and of their acid addition salts comprise:

(a) for the preparation of those compounds of formula I in which $R^1$ is hydrogen, reacting 5,7-dihydro-6H-dibenz[c,e]azepine-6-carbonitrile, that is, the cyanamide of the formula

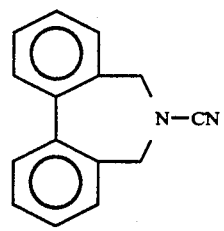

II with an alcohol or thiol of the formula $$R^{2'}-X'H \qquad \text{III}$$

wherein $R^{2'}$ and $X'$ have the significances of $R^2$ and X, respectively, given above which apply when $R^1$ is hydrogen, or with an alkali metal salt thereof, or
(b) for the preparation of those compounds of formula I in which $R^1$ is $-Y-R^3$, reacting a carboximidic acid ester of the formula

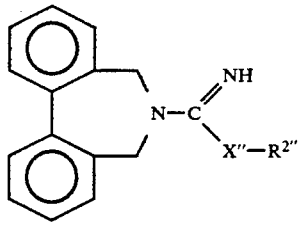

IV wherein
$R^{2''}$ and $X''$ have significances of $R^2$ and X, respectively, given above which apply when $R^1$ is $-Y-R^3$, with a carbonyl, sulfinyl or sulfonyl compound of the formula $$Q-Y-R^3 \qquad V$$

wherein
$R^3$ and Y have the significances given above and
Q is a leaving group,
and, if desired, converting a compound of formula I obtained in which $R^1$ is hydrogen by reaction with an acid into the corresponding acid addition salt.

The reaction according to process variant a) is conveniently effected using an excess of an alcohol or thiol of formula III as the solvent and in the presence of a catalytic or stoichiometric amount of an alkali metal salt, especially the sodium or potassium salt, of the alcohol or thiol of formula III. In an additional embodiment, an alcohol or thiol of formula III is used as the reaction partner and a catalytic or stoichiometric amount of alkali metal cyanide, preferably sodium or potassium cyanide. An auxiliary solvent such as an aliphatio ether, for example, dimethoxyethane or tert.butyl methyl ether, or an optionally halogenated aromatic solvent, for example, toluene or chlorobenzene, can also be used. The reaction temperatures can be varied in a wide range, generally in the range of from 10° to 120° C., preferably in the range from 40° to 100° C.

The reaction according to process variant (b) is a N-acylation, N-sulfinylation or N-sulfonylation and can be carried out under the usual reaction conditions employed for such a reaction. As compounds of formula V, the corresponding halides, especially chlorides (Q is halogen or chlorine) are preferred, but acid anhydrides $[Q-Y-R^3$ is $O(COR^3)_2]$, mixed acid anhydrides, especially those with aliphatic or aromatic carboxylic or sulfonic acids $[Q-Y-R^3$ is $O(Y'R^3)$ $(Y''R^{11})$ in which Y' and Y'' each independently are carbonyl or sulfonyl and $R^{11}$ is an aliphatic or aromatic group], as well as lower alkyl, benzyl or aryl esters, and imidazolides come into consideration.

The reaction is conveniently effected in the presence of an inert organic diluent such as an aromatic hydrocarbon, for example, benzene or toluene; an aliphatic or cyclic ether, for example, diethyl ether, tert.butyl methyl ether, tetrahydrofuran or dioxane; a halogenated aliphatic hydrocarbon, for example, methylene chloride or 1,2-dichloroethane; acetonitrile; or a dialkylamide, for example, dimethylformamide, at a temperature in the range of from −20° C. to 100° C., preferably in the range of from −10° C. to 50° C.

As a rule, a carboximidic acid ester of formula IV is reacted with a compound of formula V in the presence of an acid- binding agent such as, for example, an inorganic base, for example, potassium carbonate, or an organic base, for example, triethylamine, pyridine or quinoline, whereby any of the organic bases mentioned can simultaneously serve as the solvent.

The compounds of formula I which exist as two or more isomers are obtained, insofar as no planned synthesis for the isolation of pure isomers is carried out, in each case as a mixture of the respective isomers. The isomers can be separated according to known methods or, if desired, they can also be prepared, for example, by synthesis from the corresponding optically active starting materials. E/Z-isomeric mixtures can be separated into the pure isomers, for example, by chromatography or fractional crystallization.

For the preparation of the acid addition salts of the compounds of formula I, the compounds I are reacted with the desired acids in the usual manner, for example, by dissolving the compound of formula I in a suitable solvent and adding the acid thereto.

The isolation and the purification of the thus-obtained prepared compounds of formula I or of the acid addition salts can be effected according to known methods.

The cyanamide of formula II, which is used as the starting material in process variant a) is known, for example, from European Patent Publication No. 192,034.

In the case of the carboximidic acid esters of formula IV, which are used as starting materials in process variant (b), some are known from European Patent Publication No. 192,034 and some can be produced in accordance with process variant a). Furthermore, the compounds of formulas III and V which are used as starting materials and the alkali metal salts of the former are to a large extent known or can be produced according to known methods.

The compounds of formula I and their acid addition salts are of value as pesticides. They have been shown to be especially valuable for the control of mites, insects and nematodes, especially of mites which are of importance in plant protection such as, for example, Tetranychidae (spider mites), especially *Tetranychus urticae, Tetranychus cinnabarinus, Tetranychus turkestani, Tetranychus McDanieli, Tetranychus kanzawai;*
*Panonychus ulmi, Panonychus citri;*
*Phyllocoptruta oleivora;*
*Aculus schlechtendali;*
*Phyllocoptes vitis;*
*Aceria essigi, Aceria gracilis;*
*Cedidophyopsis ribis:*
*Eriophyes vitis; Eriophyes sheldoni, Eriophyes tulipae;*
*Eotetranychus sexmaculatus, Eotetranychus carpini;*
*Hemitarsonemus latus;*
*Acarus siro;*
*Bryobia graminum;*
mites which are of importance in veterinary medicine such as, for example,
*Macronyssus bursa, Macronyssus sylviarum, Macronyssus lacoti;*
*Dermanyssus gallinae;*
ticks, especially of the families Ixodidae and Argasidae and of the orders Boophilus, Amblyomma, Hyalomma, Rhipicephalus, Ixodes, Argas and Ornithodorus;

nematodes which are of importance in plant protection such as, for example,

Aphelenchoides sp., Globodera sp., Heliocotylenchus sp., Heterodera sp., Hoploliamus sp., Meloidoqyne sp., Paratrichodorus sp., Pratylenchus sp., Rotylenchus sp., Tylenchorhynchus sp. and Tylenchulus sp.

The compounds in accordance with the invention act as contact and feed poisons. Moreover, some of the compounds are taken up by various plants, so that the pests to be controlled are killed when they eat the plants. These compounds exhibit systemic activity.

The compounds in accordance with the invention are also active against spider mites which have developed resistance to conventional pesticides. Moreover, the compounds are characterized by a good residual activity and a good selectivity against phytoseiulus persimiles.

The pest control composition in accordance with the invention contains an effective amount of at least one compound of formula I or an acid addition salt thereof, as well as formulation adjuvants. The composition conveniently contains at least one of the following formulation adjuvants:

Solid carrier substances; solvents or dispersion media; tensides (wetting and emulsifying agents); dispersing agents (without tenside action); and stabilizers.

With the use of these and, if desired, additional adjuvants, the compounds of formula I and their acid addition salts, namely, the pesticidally active substances, can be converted into the usual formulations such as solutions, suspensions, emulsions, emulsifiable concentrates, pastes, foams, dusts, powders and granulates.

As solid carrier substances, there come into consideration: natural mineral substances such as kaolin, aluminas, siliceous earth, talc, bentonite, chalk, limestone, quartz, dolomite, attapulgite, montmorillonite and diatomaceous earth; synthetic mineral substances such as highly dispersible silicic acid, aluminum oxide and silicates; organic substances such as cellulose, starch, urea and synthetic resins; and fertilizers such as phosphates and nitrates, whereby such carrier substances can be present, for example, as dusts, powders or granulates.

As solvents or dispersion media there come into consideration: aromatics such as toluene, xylenes, benzene and alkylnaphthalenes; chlorinated aromatics and chlorinated aliphatic hydrocarbons such as chlorobenzenes, chloroethylenes and methylene chloride; aliphatic hydrocarbons such as cyclohexane and paraffins, for example, petroleum fractions; alcohols such as butanol and glycol as well as their ethers and esters; ketones such as acetone, methyl ether ketone, methyl isobutyl ketone and cyclohexanone; and strongly polar solvents such as dimethylformamide, N-methylpyrrolidone and dimethyl sulfoxide, such solvents or dispersion media preferably having flash points of at least 30° C. and boiling points of at least 50° C.; and water. As solvents or dispersion media there also come into consideration so-called liquified gaseous extenders or carrier substances, namely, products which are gaseous at room temperature and under normal pressure. Examples of such products are aerosol propellants such as halogenated hydrocarbons, for example, dichlorodifluoromethane. When water is used as the solvent, organic solvents can, for example, also be used as auxiliary solvents.

The tensides (wetting and emulsifying agents) can be non-ionic compounds such as condensation products of fatty acids, fatty alcohols or fatty-substituted phenols with ethylene oxide; fatty acid esters and ethers of sugars or polyvalent alcohols; the products which are obtained from sugars or polyvalent alcohols by condensation with ethylene oxide; block polymers of ethylene oxide and propylene oxide: or alkyldimethylamine oxides The tensides can also be anionic compdunds such as soaps; fatty sulfate esters, for example, dodecyl sodium sulfate, octadecyl sodium sulfate and cetyl sodium sulfate; alkyl sulfonates, aryl sulfonates and fatty-aromatic sulfonates such as alkylbenzene sulfonates, for example, calcium dodecylbenzenesulfonate, and butylnaphthalene sulfonates; and more complex fatty sulfonates, for example, the amide condensation products of oleic acid and N-methyltaurine and the sodium sulfonate of dioctyl succinate.

Finally, the tensides can be cationic compounds such as alkyldimethylbenzylammonium chlorides, dialkyldimethylammonium chlorides, alkyltrimethylammonium chlorides and ethoxylated quaternary ammonium chlorides.

As dispersing agents (without tenside action) there come into consideration: lignin, sodium and ammonium salts of lignin sulfonic acids, sodium salts of maleic anhydride-diisobutylene copolymers, sodium and ammonium salts of sulfonated polycondensation products of naphthalene and formaldehyde, and sulfite lyes.

As dispersing agents, which are especially suitable as thickening or anti-settling agents, there can be used, for example, methylcellulose, carboxymethylcellulose, hydroxyethylcellulose, polyvinyl alcohol, alginates, caseinates and blood albumin.

Examples of suitable stabilizers are acid-binding agents, for example, epichlorohydrin, phenyl glycidyl ether and soya epoxides; antioxidants, for example, gallic acid esters and butylhydroxytoluene; UV-absorbers, for example, substituted benzophenones, diphenylacrylonitrile acid esters and cinnamic acid esters; and deactivators, for example, salts of ethylenediaminotetraacetic acid and polyglycols.

The pest control compositions in accordance with the invention can contain, in addition to the active substances of formula I, other active substances, for example, other pest control agents, pest baits, fungicides, bactericides, plant growth regulators and fertilizers. Such combination compositions are suitable for intensifying the activity or for broadening the spectrum of activity. If desired, insufficiencies of known agents can thereby also be compensated for.

It has been found that the compounds in accordance with the invention are advantageously used in combination with conventional acaricides, especially with conventional acaricides which are suitable for the control of eggs and larvae of mites. Examples of such acaricides are chlorbenside, chlorfenson, clofentezine, fenson, fenothiocarb, flubenzimine, tetradifon, hexythiazox, benzoximate, dienochlor, flufenoxuron and NC-129. The use can be effected simultaneously or separately. Thereby, the active substances in accordance with the invention can cancel the disadvantage of known acaricides having a main focus of activity against the eggs and larvae, in that mobile stages which survive after the use of these known acaricides and which can develop rapidly to a new adult population are also killed. Since under practical conditions eggs, different larval stages as well as adults, namely male and female forms, often appear simultaneously, an overall effect which is extremely desirable in practice, that is, more rapid, more effective and longer-lasting, can be produced using combination preparations. The total amount of the two active substances in such combination preparations conveniently amounts, however, to not more than the amount of an active substance when a compound of formula I is used as the sole active substance.

The pest control compositions in accordance with the invention contain, according to type, between 0.005 and 95 weight percent of the compound or compounds in accordance with the invention as the active substance. The compounds can be present in a form which is suitable for storage and transport. In such forms, for example, emulsifiable concentrates, the active substance concentration is normally in the higher region of the above concentration range. These forms can be diluted with the same or different formulation adjuvants to give active substance concentrations which are suitable for practical use and such concentrations normally lie in the lower region of the above concentration range. Emulsifiable concentrates generally contain 5 to 90 weight percent, preferably 10 to 80 weight percent, of the compound(s) in accordance with the invention. As forms for use, there come into consideration, inter alia, ready-for-use solutions, emulsions, suspensions, foams, powders, pastes, dusting compositions and granulates. The active substance concentrations in such ready-for-use compositions can be varied in wide limits. In sprayable liquids, there can be present, for example, concentrations in the range of from 0.005 to 0.5 weight percent. In the Ultra-Low-Volume process, there can be formulated sprayable liquids in which the active substance concentration is preferably from 10 to 20 weight percent, while the spray able liquids formulated in the Low-Volume process and in the High-Volume process preferably have an active substance concentration in the range of from 0.01 to 0.5 and in the range of from 0.005 to 0.1 weight percent, respectively. Granulates preferably contain in the range of from 5 to 50 weight percent of the compound(s) in accordance with the invention as the active substance.

The pest control compositions in accordance with the invention can be prepared by mixing at least one compound of the formula I or an acid addition salt of such a compound with formulation adjuvants.

The preparation of the compositions can be carried out in a known manner, for example, by mixing the active substance with solid carrier substances, by dissolution or suspension in suitable solvents or dispersion media, if necessary using tensides as wetting or emulsifying agents, or dispersing agents, by diluting pre-prepared emulsifiable concentrates with solvents or dispersion media, and the like.

In the case of pulverous compositions, the active substance can be mixed with a solid carrier substance, for example, by grinding together; or the solid carrier substance can be impregnated with a solution or suspension of the active substance and then the solvent or suspension medium can be removed by evaporation, by heating or by suction under reduced pressure. By adding tensides or dispersing agents such pulverous compositions can be made readily wettable with water, so that they can be converted into aqueous suspensions which are suitable, for example, as spray compositions.

The compounds of formula I or their acid addition salts can also be mixed with a tenside and a solid carrier substance to form a wettable powder which is dispersible in water or they can be mixed with a solid granulated carrier substance to form a granulate.

If desired, a compound of formula I or an acid addition salt thereof can be dissolved in a water-immiscible solvent such as, for example, an alicyclic ketone, which conveniently contains a dissolved emulsifying agent, so that the solution becomes self-emulsifying upon addition to water. Alternatively, the active substance can be mixed with an emulsifying agent and the mixture can then be diluted with water to the desired concentration. Moreover, the active substance can be dissolved in a solvent and thereafter the solution can be mixed with an emulsifying agent. Such a mixture can likewise be diluted with water to the desired concentration. In this manner, there are obtained emulsifiable concentrates or ready-for-use emulsions.

The method in accordance with the invention for the control of pests comprises treating the locus to be protected or the pests themselves with an effective amount of a compound in accordance with the invention or of a pest control composition in accordance with the invention. This method of use can be carried out by application to the soil or leaves or by application to the animals, supplies or materials to be protected, depending on the kind of pests to be controlled. The control is achieved, for example, by contact or by intake with the feed.

The utilization of the compounds of formula I can be carried out in a conventional manner, for example, by sprinkling, spraying, atomizing, dusting, scattering, drilling-in, smoking, watering, steeping, coating or the like. Pulverous preparations can be applied to the pests or to the locus to be protected, for example, plants or animals, as for example, dusting agents with the aid of the usual dusting appliances. Aqueous suspensions can be used, for example, as spray compositions.

When used in plant protection, a dosage in the range of from about 100 to 500 g of active substance compound(s) of formula I]/ha, for example, as is the case in the application of 2000 l of a spray liquor which contains 0.005–0.025 weight percent of active substance to 1 ha of cultivated land, is usually sufficient.

The following Examples serve to illustrate the invention in more detail.

I. PREPARATION OF THE ACTIVE SUBSTANCES OF FORMULA I

Example 1

A mixture of 11.0 g of 5,7-dihydro-6H-dibenz[c,e]-azepine-6-carbonitrile, 11.7 g of acetone (2-hydroxyethyl) oxime and 0.33 g of potassium cyanide is heated to 85° C. for 3 days. The reaction mixture, cooled to about 40° C., is treated with 100 ml of water and extracted twice with ethyl acetate. The extracts are washed three times with water and once each time with semi-saturated and saturated sodium chloride solution, dried over anhydrous sodium sulfate and evaporated under reduced pressure. The residue is chromatographed on silica gel with acetone as the eluent, and there is obtained 2-[(isopropylideneamino)oxy]-ethyl 5,7-dihydro-6H-dibenz[c,e]azepine-6 carboximidate as an oil, mass spectrum m/e: M+337 (13), 281 (11), 237 (72), 194 (84), 179 (79), 165 (78), 100 (85), 56 (100).

In an analogous manner,
starting from 5,7-dihydro-6H-dibenz[c,e]azepine-6-carbonitrile and benzyl alcohol, there is obtained benzyl 5,7-dihydro-6H-dibenz[c,e]azepine-6-carboximidate as an oil, mas spectrum m/e: M+ 328 (4), 237 (44), 194 (100), 179 (21), 165 (30), 91 (62);

starting from 5,7-dihydro-6H-dibenz[c,e]azepine-6-carbonitrile and acetone oxime, there is obtained acetone O-[5,7-dihydro-6H-dibenz[c,e]azepin-6-yl)carboximidoyl] oxime as a syrup, mass spectrum m/e: M+ 294 (0.5), 237 (35), 220 (38), 194 (100), 179 (63), 165 (78);

starting from 5,7-dihydro-6H-dibenz[c,e]azepine-6-carbonitrile and ethyl 2-hydroxy-ethylcarbamate, there is obtained 2-ethoxycarbonylamino-ethyl 5,7-dihydro-6H-dibenz[c,e]azepine-6-carboximidate as a resinous product, mass spectrum m/e: M+ 353 (2), 308 (4), 237 (32), 194 (78), 116 (100), 88 (61);

starting from 5,7-dihydro-6H-dibenz[c,e]azepine-6-carbonitrile and m-phenoxybenzyl alcohol, there is obtained m-phenoxybenzyl 5,7-dihydro-6H-dibenz[c,e]azepine-6-carboximidate as a syrup, mass spectrum m/e:M+ 420 (14), 327 (13), 237 (35), 194 (100);

starting from 5,7-dihydro-6H-dibenz[c,e]azepine-6-carbonitrile and p-chlorobenzyl alcohol, there is obtained p-chlorobenzyl 5,7-dihydro-6H-dibenz[c,e]azepine-6-carboximidate, m.p. 103°–105° C.;

starting from 5,7-dihydro-6H-dibenz[c,e]azepine-6-carbonitrile and 2-butanone (2-hydroxyethyl) oxime, there is obtained 2-[(1-methylpropylideneamino)oxy]-ethyl 5,7-dihydro-6H-dibenz[c,e]azepine-6-carboximidate as a syrup, mass spectrum m/e: M+ 351 (23), 281 (5), 237 (57), 194 (100), 114 (100), 70 (12);

starting from 5,7-dihydro-6H-dibenz[c,e]azepine-6-carbonitrile and acetone (2-hydroxypropyl) oxime, there is obtained 2-[(isopropylideneamino)oxy]-1-methylethyl 5,7-dihydro-6H-dibenz[c,e]azepine-6-carboximidate as a syrup, mass spectrum m/e: M+ 351 (12), 295 (4), 237 (81), 194 (100), 114 (35), 56 (78);

starting from 5,7-dihydro-6H-dibenz[c,e]azepine-6-carbonitrile and methyl 2-hydroxyethylcarbamate, there is obtained 2-methoxycarbonylamino-ethyl 5,7-dihydro-6H-dibenz[c,e]azepine-6-carboximidate as a resin, mass spectrum m/e: M+ 339 (5), 308 (2), 237 (22), 194 (56), 102 (100);

starting from 5,7-dihydro-6H-dibenz[c,e]azepine-6-carbonitrile and ethyl 2-hydroxyethyl-N-methylcarbamate, there is obtained 2-(N-methyl-ethoxycarbonylamino)-ethyl 5,7-dihydro-6H-dibenz[c,e]azepine-6-carboximidate as a syrup, mass spectrum m/e: M+ 367 (2), 322 (2), 237 (6), 194 (26), 130 (100), 102 (59);

starting from 5,7-dihydro-6H-dibenz[c,e]azepine-6-carbonitrile and 2-hydroxymethyl-tetrahydrofuran, there is obtained 2-tetrahydrofurylmethyl 5,7-dihydro-6H-dibenz[c,e]azepine-6-carboximidate as a syrup, mass spectrum m/e: M+ 322 (14), 237 (66), 194 (100), 85 (36), 71 (12);

starting from 5,7-dihydro-6H-dibenz[c,e]azepine-6-carbonitrile and 2-hydroxymethyl-tetrahydropyran, there is obtained 2-tetrahydro-2H-pyranylmethyl 5,7-dihydro-6H-dibenz[c,e]azepine-6-carboximidate as a syrup, mass spectrum m/e: M+ 336 (30), 237 (78), 194 (100), 99 (60);

starting from 5,7-dihydro-6H-dibenze[c,e]azepine-6-carbonitrile and 3-phenyl-propan-1-ol, there is obtained 3-phenylpropyl 5,7-dihydro-6H-dibenz[c,e]azepine-6-carboximidate as a resin, mass spectrum m/e: M+ 356 (15), 237 (68), 194 (100), 117 (8), 91 (30);

starting from 5,7-dihydro-6H-dibenz[c,e]azepine-6-carbonitrile and 2-phenylethanol, there is obtained 2-phenylethyl 5,7-dihydro-6H-dibenz[c,e]azepine-6-carboximidate as a resin, mass spectrum m/e: M+ 342 (18), 237 (71), 194 (100), 105 (18);

starting from 5,7-dihydro-6H-dibenz[c,e]azepine-6carbonitrile and α-methylbenzyl alcohol, there is obtained α-methylbenzyl 5,7-dihydro-6H-dibenz[c,e]azepine-6-carboximidate as a resin, mass spectrum m/e: [M+ 342 (5), 237 (60), 194 (100), 105 (63);

starting from 5,7-dihydro-6H-dibenz[c,e]azepine-6-carbonitrile and 2-hydroxymethylnaphthalene, there is obtained 2-naphthylmethyl 5,7-dihydro-6H-dibenz[c,e]azepine-6-carboximidate as a resin, mass spectrum m/e: M+ 378 (19), 237 (15), 194 (90), 141 (100), 115 (53);

starting from 5,7-dihydro-6H-dibenz[c,e]azepine-6-carbonitrile and 2-phenoxyethanol, there is obtained 2-phenoxyethyl 5,7-dihydro-6H-dibenz[c,e]azepine-6-carboximidate as a resin, mass spectrum m/e: M+ 358 (20), 265 (7), 237 (65), 194 (100);

starting from 5,7-dihydro-6H-dibenz[c,e]azepine-6-carbonitrile and N-(2-hydroxyethyl)pyrrolidine, there is obtained 2-pyrrolidino-ethyl 5,7-dihydro-6H-dibenz[c,e]-azepine-6-carboximidate as a resin, mass spectrum m/e: M+ 335 (1), 238 (6), 194 (12), 179 (22), 165 (22), 97 (100), 84 (39), 69 (56);

starting from 5,7-dihydro-6H-dibenz[c,e]azepine-6carbonitrile and 1-(2-hydroxyethyl)-pyrrolidone, there is obtained 2-(2-pyrrolidinone)-ethyl 5,7-dihydro-6H-dibenz[c,e]azepine-6-carboximidate as a resin mass spectrum m/e: M+ 349 (2), 238 (20), 194 (41), 112 (100);

starting from 5,7-dihydro-6H-dibenz[c,e]azepine-6-carbonitrile and 4-(2-hydroxyethyl)-morpholine, there is obtained 2-morpholino-ethyl 5,7-dihydro-6H-dibenz[c,e]-azepine-6-carboximidate as a resin, mass spectrum m/e: M+ 351 (1), 238 (10), 113 (100);

starting from 5,7-dihydro-6H-dibenz[c,e]azepine-6-carbonitrile and 2-(2-methoxyethoxy)-ethanol, there is obtained 2-(2-methoxyethoxy)-ethyl 5,7-dihydro-6H-dibenz[c,e]azepine-6-carboximidate as a resin, mass spectrum m/e:M+ 340 (20), 237 (80), 194 (100), 59 (45).

Example 2

20 ml of 2-methoxyethanol are treated portionwise at 60° C. with 0.23 g of sodium. After 30 minutes, 2.2 g of 5,7-dihydro-6H-dibenz[c,e]azepine-6-carbonitrile are added and the mixture is stirred at 80° C. for 1 hour. Subsequently, the 2-methoxyethanol is distilled off at reduced pressure. The residue is poured on to ice-water and the resulting mixture is extracted twice with methylene chloride. The combined extracts are washed twice with water, dried over anhydrous sodium sulfate and evaporated. The residue is chromatographed on silica gel with ethyl acetate and increasing amounts of ethanol as the eluent, and there is obtained 2-methoxyethyl 5,7-dihydro-6H-dibenz[c,e]azepine-6-carboximidate as a syrup, mass spectrum m/e:M+ 296 (6), 237 (45), 194 (100), 178 (74), 165 (49).

In an analogous manner, starting from 5,7-dihydro-6H-dibenz[c,e]azepine-6-carbonitrile and hydroxymethylcyclopropane, there is obtained cyclopropylmethyl 5,7-dihydro-6H-dibenz[c,e]azepine-6-carboximidate, m.p. 80°–83° C., mass spectrum m/e: M+ 292 (2), 237 (80), 194 (100);

starting from 5,7-dihydro-6H-dibenz[c,e]azepine-6-carbonitrile and thiophenol, there is obtained phenyl 5,7-dihydro-6H-dibenz[c,e]azepine-6-thiocarboximidate as a syrup, mass spectrum m/e: M+ 330 (3), 220 (70), 179 (100), 165 (85), 110 (74);

Example 3

1.0 g of benzyl 5,7-dihydro-6H-dibenz[c,e]azepine-6-carboximidate is dissolved in 1 ml of methanol. The solution is cooled to 0° C. and treated with 0.6 ml of a 5N alcoholic hydrochloric acid solution. After stirring at 0°-5° C. for ten minutes, 10 ml of n-hexane are added, the precipitated product is removed by filtration under suction, and there is obtained benzyl 5,7-dihydro-6H-dibenz[c,e]azepine-6-carboximidate hydrochloride, m.p. 90°-92° C.

Example 4

9.32 g of ethyl 5,7-dihydro-6H-dibenz[c,e]azepine-6-carboximidate are placed in 100 ml of tert.butyl methyl ether with 3.54 g of triethylamine. 4.92 g of benzoyl chloride are added dropwise within about 30 minutes while cooling with an ice bath. The mixture is then left to stir at 0°-5° C. for 20 minutes. The reaction mixture is poured into water and extracted twice with ethyl acetate. The extracts are washed with water and saturated sodium chloride solution, dried over anhydrous sodium sulfate and evaporated. The crude product is dissolved in ethyl acetate while warming and suction filtered over an about 3 cm deep layer of silica gel. The crystals obtained after evaporation of the filtrate are recrystallized from ethanol, and there is obtained ethyl N-benzoyl-5,7-dihydro-6H-dibenz[c,e]azepine-6-carboximidate, m.p. 116°-117° C.

In an analogous manner, starting from ethyl 5,7-dihydro-6H-dibenz[c,e]azepine-6-carboximidate and p-trifluoromethylbenzoyl chloride, there is obtained ethyl N-(p-trifluoromethylbenzoyl)-5,7-dihydro-6H-dibenz[c,e]azepine-6-carboximidate, m.p. 112°-113° C.;

starting from ethyl 5,7-dihydro-6H-dibenz[c,e]azepine-6-carboximidate and p-fluorobenzoyl chloride, there is obtained ethyl N-(p-fluorobenzoyl)-5,7-dihydro-6H-dibenz[c,e]azepine-6-carboximidate, m.p. 109°-110° C.;

starting from ethyl 5,7-dihydro-6H-dibenz[c,e]azepine-6-carboximidate and p-chlorobenzoyl chloride, there is obtained ethyl N-(p-chlorobenzoyl)-5,7-dihydro-6H-dibenz[c,e]azepine-6-carboximidate, m.p. 106°-107° C.;

starting from ethyl 5,7-dihydro-6H-dibenz[c,e]azepine-6-carboximidate and p-toluoyl chloride, there is obtained ethyl N-(p-toluoyl)-5,7-dihydro-6H-dibenz[c,e]azepine-6-carboximidate as a resin, mass spectrum m/e: M+ 384 (9), 355 (15), 194 (100);

starting from ethyl 5,7-dihydro-6H-dibenz[c,e]azepine-6-carboximidate and p-anisoyl chloride, there is obtained ethyl N-(p-anisoyl)-5,7-dihydro-6H-dibenz[c,e]azepine-6-carboximidate, m.p. 71°-78° C.;

starting from 2-ethoxycarbonylamino-ethyl 5,7-dihydro-6H-dibenz[c,e]azepine-6-carboximidate and benzoyl chloride, there is obtained 2-ethoxycarbonylamino-ethyl N-benzoyl-5,7-dihydro-6H-dibenz[c,e]azepine-6-carboximidate as a resin, mass spectrum m/e: M+ 457 (6), 341 (18), 194 (100), 116 (75), 105 (75);

starting from dodecyl 5,7-dihydro-6H-dibenz[c,e]azepine-6-thiocarboximidate and benzoyl chloride, there is obtained dodecyl N-benzoyl-5,7-dihydro-6H-dibenz[c,e]-azepine-6-thiocarboximidate as a resin, mass spectrum m/e: M+ 526 (23), 357 (18), 194 (94), 105 (100);

starting from 2-[(isopropylideneamino)oxy]-ethyl 5,7-dihydro-6H-dibenz[c,e]azepine-6-carboximidate and benzoyl chloride, there is obtained 2-[(isopropylideneamino)oxy]-ethyl N-benzoyl-5,7-dihydro-6H-dibenz[c,e]-azepine-6-carboximidate as a resin, mass spectrum m/e: M+ 441 (11), 341 (39), 194 (100), 105 (60), 100 (60);

starting from ethyl 5,7-dihydro-6H-dibenz[c,e]azepine-6-carboximidate and 2,6-difluorobenzoyl chloride, there is obtained ethyl N-(2,6-difluorobenzoyl)-5,7-dihydro-6H-dibenz[c,e]azepine-6-carboximidate as a resin, mass spectrum m/e: M+ 406 (5), 377 (21), 194 (100), 141 (42);

7-dihydro-6H-dibenz[c,e]-azepine-6-carboximidate and benzoyl chloride, there is obtained methyl N-benzoyl-5,7-dihydro-6H-dibenz[c,e]-azepine-6-carboximidate, m.p. 130°-131° C.;

starting from propyl 5,7-dihydro-6H-dibenz[c,e]-azepine-6-carboximidate and benzoyl chloride, there is obtained propyl N-benzoyl-5,7-dihydro-6H-dibenz[c,e]-azepine-6-carboximidate as a resin, mass spectrum m/e: M+ 384 (7), 341 (13), 194 (100), 179 (23), 105 (59);

starting from ethyl 5,7-dihydro-6H-dibenz[c,e]azepine-6-carboximidate and 3,5-bis-(trifluoromethyl)benzoyl chloride, there is obtained ethyl N-[3,5-bis-(trifluoromethyl)-benzoyl]-5,7-dihydro-6H-dibenz[c,e]azepine-6 -carboximidate, m.p. 129°-130° C.;

starting from ethyl 5,7-dihydro-6H-dibenz[c,e]azepine-6-carboximidate and 3,4-dichlorobenzoyl chloride, there is obtained ethyl N-(3,4-dichlorobenzoyl)-5,7-dihydro-6H-dibenz[c,e]azepine-6-carboximidate, m.p. 138° C.;

starting from ethyl 5,7-dihydro-6H-dibenz[c,e]azepine-6-carboximidate and 2-furoyl chloride, there is obtained ethyl N-(2-furoyl)-5,7-dihydro-6H-dibenz[c,e]azepine-6carboximidate, m.p. 87°-92° C.;

starting from ethyl 5,7-dihydro-6H-dibenz[c,e]azepine-6-carboximidate and cyclohexanecarboxylic acid chloride, there is obtained ethyl N-cyclohexylcarbonyl-5,7-dihydro-6H-dibenz[c,e]azepine-6-carboximidate as a resin, mass spectrum m/e: M+ 376 (13), 347 (16), 293 (100), 194 (60);

starting from ethyl 5,7-dihydro-6H-dibenz[c,e]-azepine-6-carboximidate and cyclopropanecarboxylic acid chloride, there is obtained ethyl N-cyclopropylcarbonyl-5,7-dihydro-6H-dibenz[c,e]azepine-6-carboximidate, m.p. 97°-99° C.;

starting from ethyl 5,7-dihydro-6H-dibenz[c,e]azepine-6-carboximidate and biphenyl-4-carboxylic acid chloride, there is obtained ethyl N-(4-biphenylylcarbonyl)-5,7-dihydro-6H-dibenz[c,e]azepine-6-carboximidate, m.p. 52°-58° C.;

starting from ethyl 5,7-dihydro-6H-dibenz[c,e]azepine-6-carboximidate and 2,6-dichloropyridine-4-carboxylic acid chloride, there is obtained ethyl N-(2,6-dichloroisonicotinoyl)-5,7-dihydro-6H-dibenz[c,e]azepine-6-carboximidate, m.p. 151°-152° C.;

starting from ethyl 5,7-dihydro-6H-dibenz[c,e]azepine-6-carboximidate and acetyl chloride, there is obtained ethyl N-acetyl-5,7-dihydro-6H-dibenz[c,e]azepine-6-carboximidate as a syrup, mass spectrum m/e: M+ 308 (2), 279 (25), 194 (100);

starting from ethyl 5,7-dihydro-6H-dibenz[c,e]azepine-6-carboximidate and pivaloyl chloride, there is obtained ethyl N-pivaloyl-5,7-dihydro-6H-dibenz[c,e]azepine-6-carboximidate as a syrup, mass spectrum m/e: M+ 350 (2), 321 (5), 293 (100), 265 (18), 194 (29), 167 (92);

starting from ethyl 5,7-dihydro-6H-dibenz[c,e]azepine6-carboximidate and 2-trifluoromethylbenzoyl chloride, there is obtained ethyl N-(o-trifluoromethylbenzoyl)-5,7-dihydro-6H-dibenz[c,e]azepine-6-carboximidate, m.p. 122°-125° C.;

starting from ethyl 5,7-dihydro-6H-6-carboximidate and chloroacetyl chloride, there is obtained ethyl N-chloroacetyl-5,7-dihydro-6H-dibenz[c,e]-azepine-6-carboximidate, m.p. 87°-89° C.;

starting from ethyl 5,7-dihydro-6H-dibenz[c,e]azepine-6-carboximidate and 3,4-dimethoxybenzoyl chloride, there is obtained ethyl N-(3,4-dimethoxybenzoyl)-5,7-dihydro-6H-dibenz[c,e]azepine-6-carboximidate as a solid, mass spectrum m/e: M+ 430 (12), 401 (5), 194 (100), 165 (42);

starting from ethyl 5,7-dihydro-6H-dibenz[c,e]azepine-6-carboximidate and isonicotinoyl chloride, there is obtained ethyl N-(isonicotinoyl)-5,7-dihydro-6H-dibenz[c,e]azepine-6-carboximidate, m.p. 120°-122° C.;

starting from ethyl 5,7-dihydro-6H-dibenz[c,e]azepine-6-carboximidate and nicotinoyl chloride, there is obtained ethyl N-(nicotinoyl)-5,7-dihydro-6H-dibenz[c,e]azepine-6-carboximidate as a resin, mass spectrum m/e: M+ 371 (5), 42 (26), 194 (100), 106 (38);

starting from ethyl 5,7-dihydro-6H-dibenz[c,e]azepine-6-carboximidate and acryloyl chloride, there is obtained ethyl N-(acryloyl)-5,7-dihydro-6H-dibenz[c,e]azepine-6-carboximidate as a syrup, mass spectrum m/e: M+ 320 (11), 291 (19), 194 (100), 55 (15);

starting from ethyl 5,7-dihydro-6H-dibenz[c,e]azepine-6-carboximidate and 2-methylacryloyl chloride, there is obtained ethyl N-(2-methylacryloyl)-5,7-dihydro-6H-dibenz[c,e]azepine-6-carboximidate as a syrup, mass spectrum m/e: M+ 334 (20), 305 (16), 293 (7), 194 (100), 167 (29), 69 (21), 41 (30);

starting from ethyl 5,7-dihydro-6H-dibenz[c,e]azepine-6-carboximidate and p-cyanobenzoyl chloride, there is obtained ethyl N-(p-cyanobenzoyl)-5,7-dihydro-6H-dibenz[c,e]azepine-6-carboximidate as a solid, mass spectrum m/e: M+ 395 (5), 366 (24), 194 (100), 165 (18), 130 (20), 102 (14);

starting from ethyl 5,7-dihydro-6H-dibenz[c,e]azepine-6-carboximidate and 2,4-dichlorobenzoyl chloride, there is obtained ethyl N-(2,4-dichloro-benzoyl)-5,7-dihydro-6H-dibenz[c,e]azepine-6-carboximidate, m.p. 158°-159°-C.;

starting from ethyl 5,7-dihydro-6H-dibenz[c,e]azepine-6-carboximidate and sorbic acid chloride, there is obtained ethyl N-[(all-E)-2,4-hexadienoyl]-5,7-dihydro-6H-dibenz[c,e]azepine-6-carboximidate as a syrup, mass spectrum m/e: M+ 360 (13), 331 (5), 305 (10), 194 (100), 95 (25);

starting from ethyl 5,7-dihydro-6H-dibenz[c,e]azepine-6-carboximidate and cinnamoyl chloride, there is obtained ethyl N-[(E)-anisamoyl]-5,7-dihydro-6H-dibenz[c,e]azepine-6-carboximidate as a resin, mass spectrum m/e: M+ 396 (15), 367 (4), 194 (100), 131 (21);

starting from ethyl 5,7-dihydro-6H-dibenz[c,e]azepine-6-carboximidate and phenylacetyl chloride, there is obtained ethyl N-(phenylacetyl)-5,7-dihydro-6H-dibenz[c,e]azepine-6-carboximidate as a syrup, mass spectrum m/e:M+ 384 (2), 355 (1), 293 (100), 265 (15), 194 (11), 179 (26), 167 (67), 91 (20);

starting from ethyl 5,7-dihydro-6H-dibenz[c,e]azepine-6-carboximidate and 2-thienylcarbonyl chloride, there is obtained ethyl N-(2-thienylcarbonyl)-5,7-dihydro-6H-dibenz[c,e]azepine-6-carboximidate as a solid, mass spectrum m/e:M+ 376 (10), 347 (13), 194 (100), 111 (48); starting from ethyl 5,7-dihydro-6H-dibenz[c,e]azepine-6-carboximidate and 1-naphthoyl chloride, there is obtained ethyl N-(1-naphthylcarbonyl)-5,7-dihydro-6H-dibenz[c,e]azepine-6-carboximidate as a foam, mass spectrum m/e: M+ 420 (8), 391 (6), 194 (100), 155 (32), 27 (28);

starting from ethyl 5,7-dihydro-6H-dibenz[c,e]azepine-6-carboximidate and 2-naphthoyl chloride, there is obtained ethyl N-(2-naphthylcarbonyl)-5,7-dihydro-6H-dibenz[c,e]azepine-6-carboximidate as a foam, mass spectrum m/e: M+ 420 (7), 391 (8), 194 (100), 155 (28), 127 (28);

starting from ethyl 5,7-dihydro-6H-dibenz[c,e]azepine-6-carboximidate and p-tert.butylbenzoyl chloride, there is obtained ethyl N-(p-tert.butylbenzoyl)-5,7-dihydro-6H-dibenz[c,e]azepine-6-carboximidate as a foam, mass spectrum m/e: M+ 426 (8), 398 (6), 194 (100), 161 (36);

starting from ethyl 5,7-dihydro-6H-dibenz[c,e]azepine-6-carboximidate and p-bromobenzoyl chloride, there is obtained ethyl N-(p-bromobenzoyl)-5,7-dihydro-6H-dibenz[c,e]azepine-6-carboximidate, m.p. 116°-117° C.;

starting from propyl 5,7-dihydro-6H-dibenz[c,e]-azepine-6-carboximidate and p-fluorobenzoyl chloride, there is obtained propyl N-(p-fluorobenzoyl)-5,7-dihydro-6H-dibenz[c,e]azepine-6-carboximidate as a solid, mass spectrum m/e: M+ 402 (5), 359 (14), 194 (100), 123 (51);

starting from isopropyl 5,7-dihydro-6H-dibenz[c,e]-azepine-6-carboximidate and p-fluorobenzoyl chloride, there is obtained isopropyl N-(p-fluorobenzoyl)-5,7-dihydro-6H-dibenz[c,e]azepine-6-carboximidate, m.p. 90°-93° C.;

starting from methyl 5,7-dihydro-6H-dibenz[c,e]-azepine-6-carboximidate and p-fluorobenzoyl chloride, there is obtained methyl N-(p-fluorobenzoyl)-5,7-dihydro-6H-dibenz[c,e]azepine-6-carboximidate, m.p. 136°-137.5° C.;

starting from ethyl 5,7-dihydro-6H-dibenz[c,e]azepine-b 6-carboximidate and o-fluorobenzoyl chloride, there is obtained ethyl N-(o-fluorobenzoyl)-5,7-dihydro-6H-dibenz[c,e]azepine-6-carboximidate as a syrup, mass spectrum m/e: M+ 388 (6), 359 (15), 194 (100), 123 (43);

starting from ethyl 5,7-dihydro-6H-dibenz[c,e]azepine-6-carboximidate and m-fluorobenzoyl chloride, there is obtained ethyl N-(m-fluorobenzoyl)-5,7-dihydro-6H-dibenz[c,e]azepine-6-carboximidate as a syrup, mass spectrum m/e: M+ 388 (3), 359 (13), 194 (100), 123 (46), 95 (36);

starting from ethyl 5,7-dihydro-6H-dibenz[c,e]azepine-6-carboximidate and 2,4-difluorobenzoyl chloride, there is obtained ethyl N-(2,4-difluorobenzoyl)-5,7-dihydro-6H-dibenz[c,e]azepine-6-carboximidate as a syrup, mass spectrum m/e: M+ 406 (8), 377 (22), 194 (100), 141 (74);

starting from ethyl 5,7-dihydro-6H-dibenz[c,e]azepine-6-carboximidate and 2,5-difluorobenzoyl chloride, there is obtained ethyl N-(2,5-difluorobenzoyl)-5,7-dihydro-6H-dibenz[c,e]azepine-6-carboximidate as a syrup, mass spectrum m/e: M+ 406 (4), 377 (18), 194 (100), 141 (49);

starting from ethyl 5,7-dihydro-6H-dibenz[c,e]azepine-6-carboximidate and 3,4-difluorobenzoyl chloride, there is obtained ethyl N-(3,4-difluorobenzoyl)-5,7-dihydro-6H-dibenz[c,e]azepine-6-carboximidate as a resin, mass spectrum m/e: M+ 406 (3), 377 (17), 194 (100), 141 (38);

starting from ethyl 5,7-dihydro-6H-dibenz[c,e]azepine-6-carboximidate and 3,5-difluorobenzoyl chloride, there is obtained ethyl N-(3,5-difluorobenzoyl)-5,7-dihydro-6H-dibenz[c,e]azepine-6-carboximidate as a solid, mass spectrum m/e: M+ 406 (4), 377 (20), 194 (100), 141 (35);

starting from ethyl 5,7-dihydro-6H-dibenz[c,e]azepine-6-carboximidate and p-(trifluoromethoxy)-benzoyl chloride, there is obtained ethyl N-[p-(trifluoromethoxy)-benzoyl]-5,7-dihydro-6H-dibenz[c,e]azepine-6-carboximidate as a syrup, mass spectrum m/e: M+ 454 (1), 425 (11), 194 (100), 189 (40);

starting from ethyl 5,7-dihydro-6H-dibenz[c,e]azepine-6-carboximidate and o-toluoyl chloride, there is obtained ethyl N-(o-toluoyl)-5,7-dihydro-6H-dibenz[c,e]azepine-6-carboximidate as a syrup, mass spectrum: m/e: M+ 384 (5), 355 (10), 194 (100), 119 (31);

starting from ethyl 5,7-dihydro-6H-dibenz[c,e]azepine-6-carboximidate and N-morpholinecarbonyl chloride, there is obtained ethyl N-(morpholinecarbonyl)-5,7-dihydro-6H-dibenz[c,e]azepine-6-carboximidate as a resin, mass spectrum m/e: M+ 379 (12), 350 (22), 293 (77), 194 (100), 167 (98), 114 (5);

starting from acetone 0-[(5,7-dihydro-6H-dibenz[c,e]azepin-6-yl)carboximidoyl] oxime and benzoyl chloride, there is obtained N-5,7-dihydro-6H-dibenz[c,e]azepin-6-yl)[(isopropylideneamino)oxy]methylene}-benzamide as a solid, mass spectrum m/e: M+ 341 (13, M-56), 194 (100), 105 (80), 56 (44);

starting from 2-tetrahydrofurylmethyl 5,7-dihydro-6H-dibenz[c,e]azepine-6-carboximidate and benzoyl chloride, there is obtained tetrahydro-2-furfuryl N-(benzoyl)-5,7-dihydro-6H-dibenz[c,e]azepine-6-carboximidate, m.p. 158°-159° C.;

starting from 2-tetrahydro-2H-pyranylmethyl 5,7-dihydro-6H-dibenz[c,e]azepine-6-carboximidate and benzoyl chloride, there is obtained tetrahydro-2H-pyran-2-yl N-(benzoyl)-5,7-dihydro-6H-dibenz[c,e]azepine-6 carboximidate, m.p, 114.5°-117° C.;

starting from 3-pentynyl 5,7-dihydro-6H-dibenz[c,e]azepine-6-carboximidate and benzoyl chloride, there is obtained 3-pentynyl N-(benzoyl)-5,7-dihydro-6H-dibenz[c,e]azepine-6-carboximidate as a syrup, mass spectrum m/e: M+ 408 (3), 407 (4), 341 (8), 194 (100), 105 (57);

starting from ethyl 5,7-dihydro-6H-dibenz[c,e]azepine-6-carboximidate and 3,4-methylenedioxybenzoyl chloride, there is obtained ethyl N-(3,4-methylenedioxybenzoyl)-5,7-dihydro-6H-dibenz[c,e]azepine-6-carboximidate as a syrup, mass spectrum m/e: M+ 414 (5), 385 (7), 194 (100), 149 (33);

starting from ethyl 5,7-dihydro-6H-dibenz[c,e]azepine-6-carboximidate and m-toluoyl chloride, there is obtained ethyl N-(m-toluoyl)-5,7-dihydro-6H-dibenz[c,e]azepin-6-carboximidate m.p. 102°-105° C.;

starting from ethyl 5,7-dihydro-6H-dibenz[c,e]azepine-6-carboximidate and p-phenoxybenzoyl chloride, there is obtained ethyl N-(p-phenoxybenzoyl)-5,7-dihydro-6H-dibenz[c,e]azepine-6-carboximidate as a foam, mass spectrum m/e: M+ 462 (8), 433 (5), 197 (30), 194 (100);

starting from ethyl 5,7-dihydro-6H-dibenz[c,e]azepine-6-carboximidate and methoxyacetyl chloride, there is obtained ethyl N-(methoxyacetyl)-5,7-dihydro-6H-dibenz[c,e]azepine-6-carboximidate as a syrup, mass spectrum m/e: 339 (1, M+ $^{H)}$, 309 (1), 293 (98), 194 (20), 167 (100);

starting from ethyl 5,7-dihydro-6H-dibenz[c,e]azepine-6-carboximidate and methanesulfonyl chloride, there is obtained ethyl N-(methylsulfonyl)-5,7-dihydro-6H-dibenz[c,e]azepine-6-carboximidate, m.p. 136.5°-138° C.;

starting from ethyl 5,7-dihydro-6H-dibenz[c,e]azepine-6-carboximidate and benzenesulfonyl chloride, there is obtained ethyl N-(phenylsulfonyl)-5,7-dihydro-6H-dibenz[c,e]azepine-6-carboximidate, m.p. 145.5°-149.5° C.

Example 5

2.66 g of ethyl 5,7-dihydro-6H-dibenz[c,e]azepine-6-carboximidate are placed in 15 ml of methylene chloride with 1 g of triethylamine. 0.95 g of methyl chloroformate is added dropwise while cooling with an ice bath. The mixture is then left to stir at room temperature for 2 hours. The reaction mixture is poured on to ice-water and extracted twice with methylene chloride. The extracts are washed with water, dried over anhydrous sodium sulfate and evaporated under reduced pressure. The oily residue is chromatographed on silica gel with n-hexane-ethyl acetate (1:1) as the eluent, and there is obtained ethyl N-methoxycarbonyl-5,7-dihydro-6H-dibenz[c,e]azepine-6-carboximidate as an oil, mass spectrum m/e: M+ 324 (6), 295 (20), 263 (70), 194 (100), 178 (35), 165 (49).

In an analogous manner, starting from ethyl 5,7-dihydro-6H-dibenz[c,e]azepine-6-carboximidate and ethyl chloroformate, there is obtained ethyl N-ethoxycarbonyl-5,7-dihydro-6H-dibenz[c,e]azepine-6-carboximidate as an oil, mass spectrum m/e: M+ 338 (14), 309 (19), 293 (12), 263 (78), 194 (100);

starting from ethyl 5,7-dihydro-6H-dibenz[c,e]azepine-6-carboximidate and phenyl chloroformate, there is obtained ethyl N-phenoxycarbonyl-5,7-dihydro-6H-dibenz[c,e]azepine-6-carboximidate as a resin, mass spectrum m/e: 293 (100, M-phenolate radical), 265 (16), 167 (76);

starting from ethyl 5,7-dihydro-6H-dibenz[c,e]azepine-6-carboximidate and allyl chloroformate, there is obtained ethyl N-allyloxycarbonyl-5,7-dihydro-6H-dibenz[c,e]azepine-6-carboximidate, m.p. 76°-77.5° C.;

starting from ethyl 5,7-dihydro-6H-dibenz[c,e]azepine-6-carboximidate and 2-chloroethyl chloroformate, there is obtained ethyl N-(2-chloroethoxycarbonyl)-5,7-dihydro-6H-dibenz[c,e]azepine-6-carboximidate as an oil, mass spectrum m/e: M+ 372 (4), 343 (12), 293 (10), 263 (72), 194 (100), 178 (86), 165 (79);

starting from ethyl 5,7-dihydro-6H-dibenz[c,e]azepine-6carboximidate and benzyl chloroformate, there is obtained ethyl N-benzyloxycarbonyl-5,7-dihydro-6H-dibenz[c,e]azepine-6-carboximidate as a syrup, mass spectrum m/e:M+ 400 (6), 371 (6), 309 (32), 263 (20), 194 (35), 179 (15), 167 (27), 108 (12), 91 (100);

starting from ethyl 5,7-dihydro-6H-dibenz[c,e]azepine-6-carboximidate and butyl chloroformate, there is obtained ethyl N-butoxycarbonyl-5,7-dihydro-6H-dibenz[c,e]azepine-6-carboximidate as a syrup, mass spectrum m/e: M+ 366 (6), 337 (10), 293 (12), 263 (67), 194 (100);

starting from ethyl 5,7-dihydro-6H-dibenz[c,e]azepine-6-carboximidate and isobutyl chloroformate, there is obtained ethyl N-isobutoxycarbonyl-5,7-dihydro-6H-dibenz[c,e]azepine-6-carboximidate as a syrup, mass spectrum m/e: M+ 366 (11), 337 (13), 293 (20), 263 (88), 194 (100);

starting from ethyl 5,7-dihydro-6H-dibenz[c,e]azepine-6-carboximidate and propyl chloroformate, there is obtained ethyl N-propoxycarbonyl-5,7-dihydro-6H- dibenz[c,e]azepine-6-carboximidate as a syrup, mass spectrum m/e: M+ 352 (8), 323 (14), 293 (14), 263 (78), 194 (100).

Example 6

2.0 g of ethyl 5,7-dihydro-6H-dibenz[c,e]azepine-6-carboximidate are placed in 10 ml of methylene chloride. After the addition of one drop of triethylamine, 0.41 g of methyl isocyanate in 5 ml of methylene chloride is added dropwise. The mixture is then left to stir at room temperature for 2 days. The reaction mixture is poured on to ice-water and extracted twice with methylene chloride. The extracts are washed with water, dried over anhydrous sodium sulfate and evaporated under reduced pressure. The oily residue is chromatographed on silica gel with n-hexane-acetone (4:1) as the eluent, and there is obtained ethyl 5,7-dihydro-N-methylcarbamoyl-6H-dibenz[c,e]azepine-6-carboximidate in 2 isomeric forms: isomer A (eluted first), m.p. 176°–178° C.; isomer B: m.p. 137°–139° C.

In an analogous manner, starting from ethyl 5,7-dihydro-6H-dibenz[c,e]-azepine-6-carboximidate and p-chlorophenyl isocyanate, there is obtained ethyl N-[(p-chlorophenyl)carbamoyl]-5,7-dihydro-6H-dibenz[c,e]azepine-6-carboximidate, m.p. 154°–156° C.;

starting from ethyl 5,7-dihydro-6H-dibenz[c,e]azepine-6-carboximidate and p-(trifluoromethoxy)-phenyl isocyanate, there is obtained ethyl N-{[p-(trifluoromethoxy)-phenyl]carbamoyl}-5,7-dihydro-6H-dibenz[c,e]azepine-6 -carboximidate, m.p. 129°–130° C.

Example 7

2.0 g of ethyl 5,7-dihydro-6H-dibenz[c,e]azepine-6carboximidate and 1.83 g of 1,1'-carbonyldiimidazole are stirred at room temperature for 5 hours in 20 ml of tetrahydrofuran. The reaction mixture is poured into water and extracted twice with ethyl acetate. The extracts are washed with saturated sodium chloride solution, dried over anhydrous sodium sulfate and evaporated. The residue is chromatographed on silica gel with n-hexane/acetone (1:4) as the eluent, and there is obtained ethyl N-(1-imidazolylcarbonyl)-5,7-dihydro-6H-dibenz[c,e]azepine-6 carboximidate, m,p. 134°–137° C.

II. FORMULATION EXAMPLES

Example 8

A spray powder has the following composition:

| | Weight percent |
|---|---|
| Compound of formula I or an acid addition salt thereof (active substance) | 50 |
| Hydrated silicic acid (carrier substance) | 37 |
| Sodium polycarboxylate (dispersing agent) | 4 |
| Nonylphenyl-(10)ethoxylate (wetting agent) | 4 |
| Kaolin (carrier substance) | 5 |
| | 100 |

The active substance is mixed with the kaolin. Separately, the wetting agent is taken up on the hydrated silicic acid and the dispersing agent is added. The whole is then mixed homogeneously and finely ground in a suitable mill. The resulting spray powder is spontaneously wetted by water which gives a ready-for-use dispersion.

Example 9

An emulsifiable concentrate has the following composition:

| | g/liter |
|---|---|
| A compound of formula I (active substance) | 250 |
| Polyarylphenol-(18)ethoxylate (emulsifier) | 300 |
| Isoterdecyl alcohol (antifoam agent) | 20 |
| Polyvinylpyrrolidone (dispersing agent) | 20 |
| N-Methyl-pyrrolidone (solvent) | ad 1000 ml |

The active substance, the emulsifier and the antifoam agent are taken up in the solvent while stirring. Thereupon, the dispersing agent is added and dissolved while stirring. After dilution with water, the thus-obtained emulsifiable concentrate gives an emulsion which is suited as a ready-for-use spray liquid.

I claim:

1. A compound of the formula

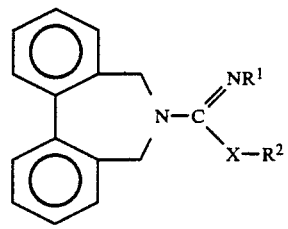

I wherein $R^1$ is hydrogen or —Y—$R^3$, $R^2$ is $C_{1-6}$-alkyl, $C_{3-6}$-alkenyl or $C_{3-6}$-alkynyl substituted with $C_{36}$-cycloalkyl, aryl, aryloxy or heteroaryl, when $R^1$ is hydrogen, or, when $R^1$ is —Y—$R^3$, $R^2$ is unsubstituted $C_{1-6}$-alkyl, $C_{1-6}$-alkyl, $C_{3-6}$-alkenyl or $C_{3-6}$-alkynyl or substituted with $C_{3-6}$-cycloalkyl, aryl, aryloxy or heteroaryl, or $R^2$ is unsubstituted $C_{2-6}$-alkyl or substituted with aryl or aryloxy and which is interrupted by one or two oxygen atoms, or $R^2$ is aryl, heteroaryl, 2-tetrahydrofuranylmethyl, 2-tetrahydropyranylmethyl or one of the groups (a) to (c)

—N=CR$^4$R$^5$     (a)

—Z—ON=CR$^4$R$^5$     (b)

—Z—NR$^6$R$^7$     (c)

$R^3$ is hydrogen; unsubstituted $C_{1-6}$-alkyl, $C_{2-6}$-alkenyl, $C_{2-6}$-alkynyl, $C_{3-6}$-cycloalkyl, phenyl, naphthyl, p-biphenylyl, benzylphenyl, phenoxyphenyl, benzoylphenyl, 3,4-methylenedioxyphenyl or five- to six-membered heterocyclyl; a group —OR$^8$ (d); or a group (e), $R^4$ is $C_{1-6}$-alkyl, $R^5$ is $C_{1-6}$-alkyl or phenyl, or $R^4$ and $R^5$ taken together are tetra-, penta- or hexamethylene, $R^6$ is hydrogen or $C_{1-4}$-alkyl, $R^7$ is $C_{1-4}$-alkyl, $C_{2-5}$-alkanoyl or $C_{2-5}$-alkoxycarbonyl, or $R^6$ and $R^7$ taken together with the nitrogen atom to which they are attached are a five- to seven-membered unsubstituted heterocyclic group or substituted with one or two $C_{1-4}$-alkyl groups and which, in addition to the nitrogen, can also have an additional 1 or 2 hetero atoms selected from the group consisting of oxygen, sulfur and nitrogen, and/or has a keto function in the ring, $R^8$ is $C_{1-6}$-alkyl, $C_{2-6}$-haloalkyl, $C_{3-6}$-alkenyl, $C_{3-6}$-alkynyl, benzyl or unsubstituted or substituted phenyl, $R^9$ is hydrogen or $C_{1-4}$-alkyl, $R^{10}$ is $C_{1-6}$-alkyl or unsubstituted or substituted phenyl, X is oxygen or sulfur, provided that when $R^2$ is group (a), X is oxygen, Y is carbonyl, sulfinyl or sulfonyl, provided that when $R^3$ is hydrogen or a group (d) or (e), Y is carbonyl, and Z is $C_{1-4}$-alkylene, or an acid addition salt thereof, when $R^1$ is hydrogen.

2. A compound in accordance with claim 1, wherein $R^3$ is hydrogen; unsubstituted or substituted $C_{1-6}$-alkyl, $C_{3-6}$-alkenyl, $C_{3-6}$-alkYnyl, $C_{3-6}$-cycloalkyl, phenyl, naphthyl, p-biphenylyl, benzylphenyl, phenoxyphenyl, benzoylphenyl or five- to six-membered heterocyclyl; a group $-OR^8$ (d) wherein $R^8$ is $C_{1-6}$-alkyl or unsubstituted or substituted phenyl; or a group $-NR^9R^{10}$ (e).

3. A compound in accordance with claim 2, wherein $R^1$ is $-Y-R^3$.

4. A compound in accordance with claim 3, wherein X is oxygen.

5. A compound in accordance with claim 1, wherein $R^1$ is hydrogen, $R^2$ is a group ((b) or (c) and Z is ethylene.

6. A compound in accordance with claim 3, wherein $R^2$ is $C_{1-4}$-alkyl, $R^3$ is unsubstituted or substituted phenyl, unsubstituted or substituted five- to six-membered heterocyclyl or group (d) and Y is carbonyl.

7. A compound in accordance with claim 1, selected from the group consisting of:

2-[(Isopropylideneamino)oxy]-ethyl 5,7-dihydro-6H-dibenz[c,e]azepine-6-carboximidate, 2-ethoxycarbonylamino-ethyl 5,7-dihydro-6H-dibenz[c,e]azepine-6-carboximidate, ethyl N-benzoyl-5,7-dihydro-6H-dibenz[c,e]azepine-6carboximidate, ethyl N-(p-chlorobenzoyl)-5,7-dihydro-6H-dibenz[c,e]azepine-6-carboximidate, ethyl N-isonicotinoyl-5,7-dihydro-6H-dibenz[c,e]azepine-6-carboximidate, ethyl N-ethoxycarbonyl-5,7-dihydro-6H-dibenz[c,e]azepine -6-carboximidate, ethyl N-(1-imidazolylcarbonyl)-5,7-dihydro-6H-dibenz[c,e]azepine-6-carboximidate, ethyl N-(p-bromobenzoyl)-5,7-dihydro-6H-dibenz[c,e]azepine-6-carboximidate, ethyl N-(p-tert.butylbenzoyl)-5,7-dihydro-6H-dibenz[c,e]azepine-6-carboximidate, ethyl N-(p-fluorobenzoyl)-5,7-dihydro-6H-dibenz[c,e]azepine-6-carboximidate, ethyl N-methoxycarbonyl-5,7-dihydro-6H-dibenz[c,e]azepine-6-carboximidate, cyclopropylmethyl 5,7-dihydro-6H-dibenz[c,e]azepine-6-carboximidate, ethyl N-(p-trifluoromethylbenzoyl)-5,7-dihydro-6H-dibenz[c,e]azepine-6-carboximidate, ethyl N-(p-anisoyl)-5,7-dihydro-6H-dibenz[c,e]azepine-6-carboximidate, methyl N-benzoyl-5,7-dihydro-6H-dibenz[c,e]azepine-6-carboximidate, propyl N-benzoyl-5,7-dihydro-6H-dibenz[c,e]azepine-6-carboximidate, ethyl N-(2-furoyl)-5,7-dihydro-6H-dibenz[c,e]azepine-6-carboximidate, and ethyl N-cyclopropylcarbonyl-5,7-dihydro-6H-dibenz[c,e]azepine-6-carboximidate.

8. A pest control composition which contains an effective amount of one or more compounds of the formula

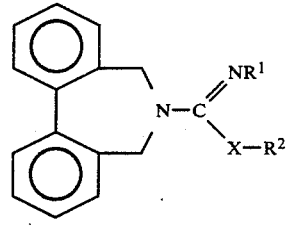

I wherein $R^1$ is hydrogen or $-Y-R^3$, $R^2$ is $C_{1-6}$-alkyl, $C_{3-6}$-alkenyl or $C_{3-6}$alkynyl substituted with $C_{3-6}$-cycloalkyl, aryl, aryloxy or heteroaryl, when $R^1$ is hydrogen, or, when $R^1$ is $-Y-R^3$, $R^2$ is unsubstituted $C_{1-6}$-alkyl, $C_{3-6}$-alkenyl or $C_{3-6}$-alkynyl or substituted with $C_{3-6}$-cycloalkyl, aryl, aryloxy or heteroaryl, or $R^2$ is unsubstituted $C_{2-6}$-alkyl or substituted with aryl or aryloxy and which is interrupted by one or two oxygen atoms, or $R^2$ is aryl, heteroaryl, 2-tetrahydrofuranylmethyl, 2-tetrahydropyranylmethyl or one of the groups (a) to (c)

$-N=CR^4R^5$          (a)

$-Z-ON=CR^4R^5$          (b)

$-Z-NR^6R^7$          (c)

$R^3$ is hydrogen; unsubstituted or substituted $C_{1-6}$-alkyl, $C_{2-6}$-alkenyl, $C_{2-6}$-alkynyl, $C_{3-6}$-cycloalkyl, phenyl, naphthyl, p-biphenylyl, benzylphenyl, phenoxyphenyl, benzoylphenyl, 3,4-methylenedioxyphenyl or five- to six-membered heterocyclyl; a group $-OR^8$ (d); or a group $-NR^9R^{10}$ (e), $R^4$ is $C_{1-6}$-alkyl, $R^5$ is $C_{1-6}$-alkyl or phenyl, or $R^4$ and $R^5$ taken together are tetra-, penta- or hexamethylene, $R^6$ is hydrogen or $C_{1-4}$-alkyl, $R^7$ is $C_{1-4}$-alkyl, $C_{2-5}$-alkanoyl or $C_{2-5}$-alkoxycarbonyl, or $R^6$ and $R^7$ taken together with the nitrogen atom to which they are attached are a five- to seven-membered unsubstituted heterocyclic group or substituted with one or two $C_{1-4}$-alkyl groups and which, in addition to the nitrogen, can also have an additional 1 or 2 hetero atoms selected from the group consisting of oxygen, sulfur and nitrogen, and/or has a keto function in the ring, $R^8$ is $C_{1-6}$-alkyl, $C_{2-6}$-haloalkyl, $C_{3-6}$-alkenyl, $C_{3-6}$-alkynyl, benzyl or unsubstituted or substituted phenyl, $R^9$ is hydrogen or $C_{1-4}$-alkyl, $R^{10}$ is $C_{1-6}$-alkyl or unsubstituted or substituted phenyl, X is oxygen or sulfur, provided that when $R^2$ is group (a), X is oxygen, Y is carbonyl, sulfinyl or sulfonyl, provided that when $R^3$ is hydrogen or a group (d) or (e), Y is carbonyl, and Z is $C_{1-4}$-alkylene, or an acid addition salt thereof, when $R^1$ is hydrogen, and one or more formulation adjuvants.

9. A pest control composition in accordance with claim 8, wherein $R^3$ is hydrogen; unsubstituted or substituted $C_{1-6}$-alkyl, $C_{3-6}$-alkenyl, $C_{3-6}$-alkynyl, $C_{3-6}$-cycloalkyl, phenyl, naphthyl, p-biphenylyl, benzylphenyl, phenoxyphenyl, benzoylphenyl, or five- to six-membered heterocyclyl; a group —$OR^8$ (d) wherein $R^8$ is $C_{1-6}$-alkyl or unsubstituted or substituted phenyl; or a group —$NR^9R^{10}$ (e).

10. A pest control composition in accordance with claim 9, wherein $R^1$ is —Y—$R^3$.

11. A pest control composition in accordance with claim 10, wherein X is oxygen.

12. A pest control composition in accordance with claim 8, wherein $R^1$ is hydrogen, $R^2$ is group ((b) or (c) and Z is ethylene.

13. A pest control composition in accordance with claim 10, wherein $R^2$ is $C_{1-4}$-alkyl, $R^3$ is unsubstituted or substituted phenyl, unsubstituted or substituted five- to six-membered heterocyclyl or group (d) and Y is carbonyl.

14. A pest control composition in accordance with claim 8, which contains an effective amount of one or more compounds of formula I which are selected from the group consisting of 2-[(isopropylideneamino)oxy]-ethyl 5,7-dihydro-6H-dibenz[c,e]azepine-6-carboximidate, 2-ethoxycarbonylamino-ethyl 5,7-dihydro-6H-dibenz[c,e]azepine-6-carboximidate, ethyl N-benzoyl-5,7-dihydro-6H-dibenz[c,e]azepine-6-carboximidate, ethyl N-(p-chlorobenzoyl)-5,7-dihydro-6H-dibenz[c,e]azepine-6-carboximidate, ethyl N-isonicotinoyl-5,7-dihydro-6H-dibenz[c,e]azepine-6carboximidate, ethyl N-ethoxycarbonyl-5,7-dihydro-6H-dibenz[c,e]azepine-6-carboximidate, ethyl N-(1-imidazolylcarbonyl)-5,7-dihydro-6H-dibenz[c,e]azepine-6-carboximidate, ethyl N-(p-bromobenzoyl)-5,7-dihydro-6H-dibenz[c,e]azepine-6-carboximidate, ethyl N-(p-tert.butylbenzoyl)-5,7-dihydro-6H-dibenz[c,e]azepine-6-carboximidate, ethyl N-(p-fluorobenzoyl)-5,7-dihydro-6H-dibenz[c,e]azepine-6-carboximidate, ethyl N-methoxycarbonyl-5,7-dihydro-6H-dibenz[c,e]azepine-6-carboximidate, cyclopropylmethyl 5,7-dihydro-6H-dibenz[c,e]azepine-6-carboximidate, ethyl N-(p-trifluoromethylbenzoyl)-5,7-dihydro-6H-dibenz[c,e]azepine-6-carboximidate, ethyl N-(p-anisoyl)-5,7-dihydro-6H-dibenz[c,e]azepine-6-carboximidate, methyl N-benzoyl-5,7-dihydro-6H-dibenz[c,e]azepine-6-carboximidate, propyl N-benzoyl-5,7-dihydro-6H-dibenz[c,e]azepine-6-carboximidate, ethyl N-(2-furoyl)-5,7-dihydro-6H-dibenz[c,e]azepine-6-carboximidate, and ethyl N-cyclopropylcarbonyl-5,7-dihydro-6H-dibenz[c,e]azepine-6-carboximidate.

15. A method for the control of pests which comprises treating the locus to be protected or the pests themselves with an effective amount of one or more compounds of the formula

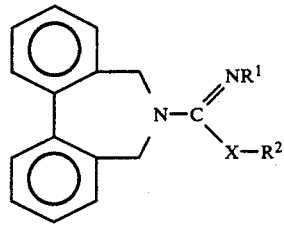

I wherein $R^1$ is hydrogen or —Y—$R^3$, $R^2$ is $C_{1-6}$-alkyl, $C_{3-6}$-alkenyl or $C_{3-6}$-alkynyl substituted with $C_{3-6}$-cycloalkyl, aryl, aryloxy or heteroaryl, when $R^1$ is hydrogen, or, when $R^1$ is —Y—$R^3$, $R^2$ is unsubstituted $C_{1-6}$-alkyl, $C_{3-6}$-alkenyl or $C_{3-6}$-alkynyl or substituted with $C_{3-6}$-cycloalkyl, aryl, aryloxy or heteroaryl, or is unsubstituted $C_{2-6}$-alkyl or substituted with aryl or aryloxy and which is interrupted by one or two oxygen atoms, or $R^2$ is aryl, heteroaryl, 2-tetrahydrofuranylmethyl, 2-tetrahydropyranylmethyl or one of the groups (a) to (c)

$$—N=CR^4R^5 \quad (a)$$

$$—Z—ON=CR^4R^5 \quad (b)$$

$$—Z—NR^6R^7 \quad (c)$$

$R^3$ is hydrogen; unsubstituted or substituted $C_{1-6}$-alkyl, $C_{2-6}$-alkenyl, $C_{2-6}$-alkynyl, $C_{3-6}$-cycloalkyl, phenyl, naphthyl, p-biphenylyl, benzylphenyl, phenoxyphenyl, benzoylphenyl, 3,4-methylenedioxyphenyl or five- to six-membered heterocyclyl; a group —$OR^8$ (d); or a group —$NR^9R^{10}$ (e), $R^4$ is $C_{1-6}$-alkyl, $R^5$ is $C_{1-6}$-alkyl or phenyl, or $R^4$ and $R^5$ taken together are tetra-, penta- or hexamethylene, $R^6$ is hydrogen or $C_{1-4}$-alkyl, $R^7$ is $C_{1-4}$-alkyl, C2-5-alkanoyl or C2-5-alkoxycarbonyl, or $R^6$ and $R^7$ taken together with the nitrogen atom to which they are attached are a five- to seven-membered unsubstituted heterocyclic group or substituted with one or two $C_{1-4}$-alkyl groups and which, in addition to the nitrogen, can also have an additional 1 or 2 hetero atoms selected from the group consisting of oxygen, sulfur and nitrogen, and/or has a keto function in the ring, $R^8$ is $C_{1-6}$-alkyl, $C_{2-6}$-haloalkyl, $C_{3-6}$-alkenyl, $C_{3-6}$-alkynyl, benzyl or unsubstituted or substituted phenyl, $R^9$ is hydrogen or $C_{1-4}$-alkyl, $R^{10}$ is $C_{1-6}$-alkyl or unsubstituted or substituted phenyl, X is oxygen or sulfur, provided that when $R^2$ is group (a), X is oxygen, Y is carbonyl, sulfinyl or sulfonyl, provided that $R^3$ is hydrogen or a group (d) or (e), Y is carbonyl, and Z is $C_{1-4}$-alkylene, or an acid addition salt thereof, when $R^1$ is hydrogen.

16. A method in accordance with claim 15, wherein $R^3$ is hydrogen; unsubstituted or substituted $C_{1-6}$-alkyl, $C_{3-6}$-alkenyl, $C_{3-6}$-alkynyl, $C_{3-6}$-cycloalkyl, phenyl, naphthyl, p-biphenylyl, benzylphenyl, phenoxyphenyl, benzoylphenyl or five- to six-membered heterocyclyl; a group —$OR^8$ (d) wherein $R^8$ is $C_{1-6}$-alkyl or unsubstituted or substituted phenyl; or a group —$NR^9R^{10}$ (e).

17. A method in accordance with claim 16, wherein $R^1$ is —Y—$R^3$.

18. A method in accordance with claim 17, wherein X is oxygen.

19. A method in accordance with claim 15, wherein $R^1$ is hydrogen, $R^2$ is a group ((b) or (c) and Z is ethylene.

20. A method in accordance with claim 17, wherein $R^2$ is $C_{1-4}$-alkyl, $R^3$ is unsubstituted or substituted phenyl, unsubstituted or substituted five- to six-membered heterocyclyl or group (d) and Y is carbonyl.

21. A method in accordance with claim 15, which utilizes an effective amount of one or more compounds of formula I which are selected from the group consisting of:

2-[(Isopropylideneamino)oxy]-ethyl 5,7-dihydro-6H-dibenz[c,e]azepine-6-carboximidate, 2-ethoxycarbonylamino-ethyl 5,7-dihydro-6H-dibenz[c,e]azepine-6-carboximidate, ethyl N-benzoyl-5,7-dihydro-6H-dibenz[c,e]azepine-6-carboximidate, ethyl N-(p-chlorobenzoyl)-5,7-dihydro-6H-dibenz[c,e]azepine-6-carboximidate, ethyl N-isonicotinoyl-5,7-dihydro-6H-dibenz[c,e]azepine-6-carboximidate, ethyl N-ethoxycarbonyl-5,7-dihydro-6H-dibenz[c,e]azepine-6-carboximidate, ethyl N-(1-imidazolylcarbonyl)-5,7-dihydro-6H-dibenz[c,e]azepine-6-carboximidate, ethyl N-(p-bromobenzoyl)-5,7-dihydro-6H-dibenz[c,e]azepine-6-carboximidate, ethyl N-(p-tert.butylbenzoyl)-5,7-dihydro-6H-dibenz[c,e]azepine-6-carboximidate, ethyl N-(p-fluorobenzoyl)-5,7-dihydro-6H-dibenz[c,e]azepine-6-carboximidate, ethyl N-methoxycarbonyl-5,7-dihydro-6H-dibenz[c,e]azepine-6-carboximidate, cyclopropylmethyl 5,7-dihydro-6H-dibenz[c,e]azepine-6-carboximidate, ethyl N-(p-trifluoromethylbenzoyl)-5,7-dihydro-6H-dibenz[c,e]azepine-6-carboximidate, ethyl N-(p-anisoyl)-5,7-dihydro-6H-dibenz[c,e]azepine-6-carboximidate, methyl N-benzoyl-5,7-dihydro-6H-dibenz[c,e]azepine-6carboximidate, propyl N-benzoyl-5,7-dihydro-6H-dibenz[c,e]azepine-6-carboximidate, ethyl N-(2-furoyl)-5,7-dihydro-6H-dibenz[c,e]azepine-6-carboximidate, and ethyl N-cyclopropylcarbonyl-5,7-dihydro-6H-dibenz[c,e]azepine-6-carboximidate.

22. A compound in accordance with claim 6, wherein the heterocyclyl is pyridyl, pyrrolyl, piperidinyl, pyrazinyl, imidazoly, 1,2,4-triazolyl, furyl, thiophenyl, morpholinyl, quinolinyl or benzofuryl.

23. A compound in accordance with claim 1, wherein $R^2$ is pyridyl, furyl, thienyl, quinolinyl or quinoxalinyl.

24. A pest control composition in accordance with claim 13, wherein the heterocyclyl is pyridyl, pyrrolyl, piperidinyl, pyrazinyl, imidazolyl, 1,2,4-triazolyl, furyl, thiophenyl, morpholinyl, quinolinyl or benzofuryl.

25. A pest control composition in accordance with claim 8, wherein $R^2$ is pyridyl, furyl, thienyl, quinolinyl or quinoxalinyl.

26. A method in accordance with claim 20, wherein the heterocyclyl is pyridyl, pyrrolyl, piperidinyl, pyrazinyl, imidazolyl, 1,2,4-triazolyl, furyl, thiophenyl, morpholinyl, quinolinyl, or benzofuryl.

27. A method in accordance with claim 15, wherein $R^2$ is pyridyl, furyl, thienyl, quinolinyl or quinoxalinyl.

* * * * *